United States Patent [19]

Hauser et al.

[11] Patent Number: 4,515,720
[45] Date of Patent: May 7, 1985

[54] METHOD OF SYNTHESIZING A LATE-STAGE INTERMEDIATE TO 11-DEOXYDAUNORUBICIN AND 11-DEOXYADRIAMYCIN, AND TWO PRECURSORS TO THE OBJECT INTERMEDIATE

[75] Inventors: Frank M. Hauser, Portland; Dipakranjan Mal, Beaverton, both of Oreg.

[73] Assignee: Oregon Graduate Center for Study & Research, Beaverton, Oreg.

[21] Appl. No.: 474,491

[22] Filed: Mar. 11, 1983

[51] Int. Cl.$^3$ ...................... C07C 50/22; C07C 50/36
[52] U.S. Cl. .............................. 260/351.1; 260/351.5; 260/365; 260/376
[58] Field of Search ..................... 260/376, 365, 351.1, 260/351.5

[56] References Cited

U.S. PATENT DOCUMENTS 4,215,062  7/1980  Mitscher .............................. 260/376
4,244,880  1/1981  Alexander et al. ................. 260/376
4,264,510  4/1981  Vogel et al. ........................ 260/376

FOREIGN PATENT DOCUMENTS 9038 of 1903 United Kingdom ............... 260/365

Primary Examiner—Glennon H. Hollrah
Assistant Examiner—Raymond Covington
Attorney, Agent, or Firm—Kolisch, Hartwell Dickinson & Anderson

[57] ABSTRACT

Preparation of 9-acetyl-6-hydroxy-4-methoxy-7,8,9,10-tetrahydronaphthacene-5,12-dione (the object intermediate), and precursor compounds to the object intermediate. Preparation of the object intermediate according to the invention begins from 2-(2-hydroxyethyl)-bicyclo[2.2.2]oct-5-ene, wherein the latter is converted to 6-acetyl-4a,5,6,7,8,8a-hexahydro-1(4H) naphthalenone (one of the two precursor compounds) which is subsequently reacted with a phenylsulfonyl isobenzofuranone to furnish, regiospecifically, 9-acetyl-5,12-dihydroxy-4-methoxy-6(11H)-hexahydronaphthacenone (the other of the two precursor compounds). Heating the hexahydronaphthacenone in dimethylforamide under an oxygen atmosphere gives the object intermediate.

3 Claims, 8 Drawing Figures

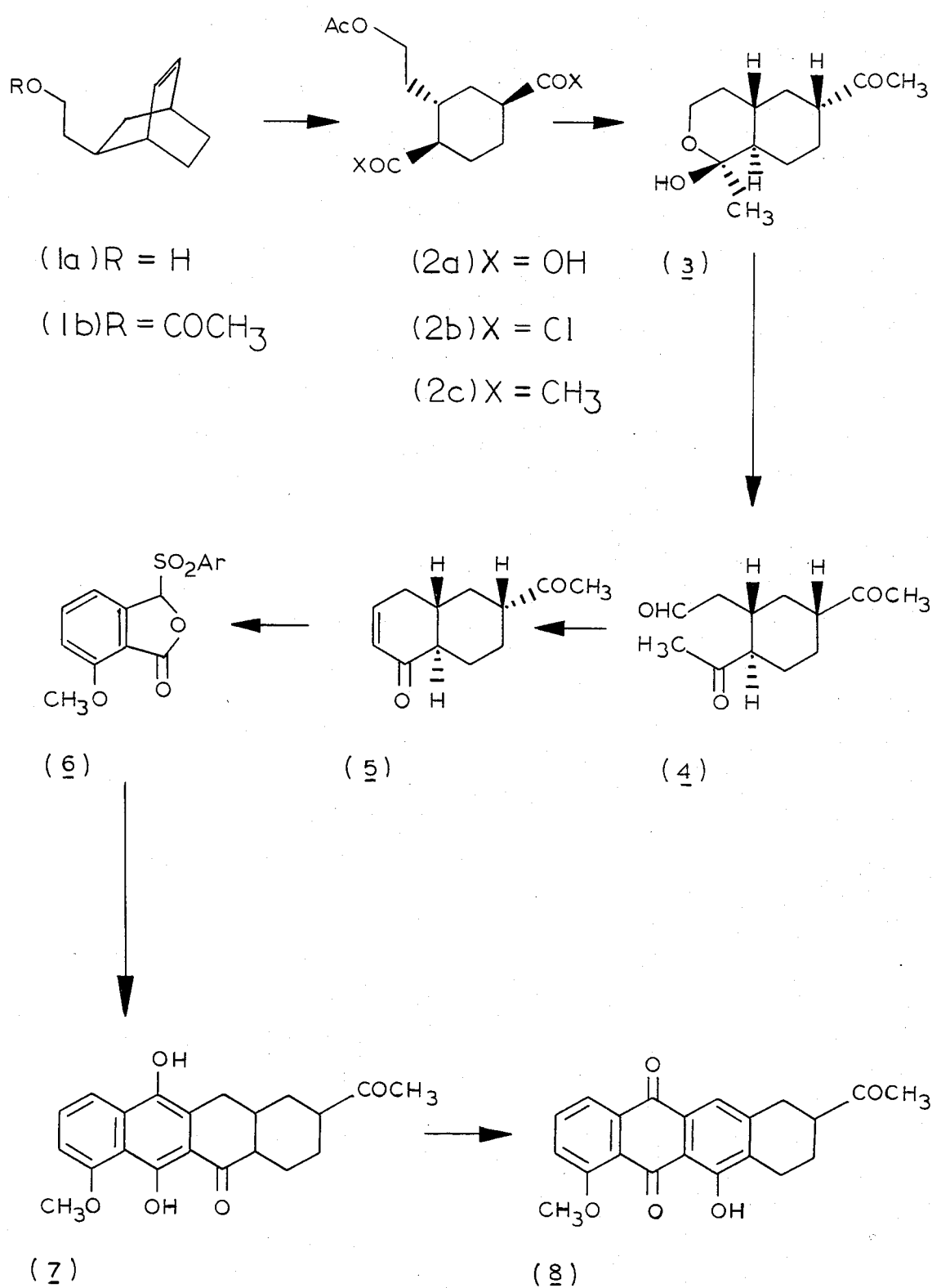

METHOD OF SYNTHESIZING A LATE-STAGE INTERMEDIATE TO 11-DEOXYDAUNORUBICIN AND 11-DEOXYADRIAMYCIN, AND TWO PRECURSORS TO THE OBJECT INTERMEDIATE

BACKGROUND AND SUMMARY OF THE INVENTION

The work leading to the invention disclosed herein was generously supported by the National Cancer Institute (CA 18141) and by a Career Development Award to Dr. Frank M. Hauser (CA 0.00487).

The present invention relates to the production, from readily prepared starting materials, of 9-acetyl-6-hydroxy-4-methoxy-7,8,9,10-tetrahydronaphthacene-5,12-dione—an established late-stage intermediate to 11-deoxydaunorubicin and to 11-deoxyadriamycin. Further, it relates to two precursor compounds which have special utility in the synthesis of the object intermediate: 6-acetyl-4a,5,6,7,8,8a-hexahydro-1(4H)-naphthalenone, and 9-acetyl-5,12-dihydroxy-4-methoxy-6(11H)-hexahydronaphthacenone.

The object intermediate, tetrahydronaphthacene dione, can be represented by the following diagram:

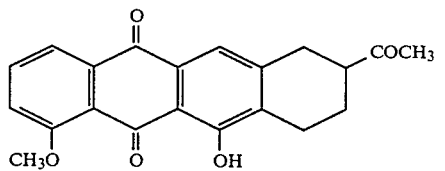

The hexahydronaphthalenone precursor can be represented as:

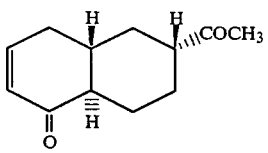

The hexahydronaphthacenone precursor can be represented as:

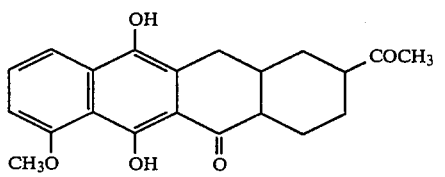

The anthracycline antibiotics 11-deoxydaunorubicin and 11-deoxyadriamycin, 11-deoxy analogs of the therapeutically useful anthracycline antibiotics daunorubicin and adriamycin, were isolated by Arcamone et al., J. Am. Chem. Soc. 1980, 102, 1462, from microorganisms. While these 11-deoxy compounds are somewhat less active as anticancer agents than either daunorubicin or adriamycin, they exhibit significantly less cardiotoxicity, and are potentially important compounds for the treatment of various cancers.

In view of the high cost of producing these antibiotics microbiologically, various attempts to develop effective synthetic routes for their production have been reported. Particular emphasis, for example, has been placed on preparing the aglycone fragment which can be coupled with daunosamine, the amino sugar fragment, to furnish the parent antibiotic. Syntheses of the aglycone have been reported by Sih et al., Tetrahedron Lett. 1980, 21, 3351; Rapoport et al., Tetrahedron Lett. 1980, 21, 4777; Mondon et al., Tetrahedron Lett. 1980, 21, 3351; J. Chem. Soc. Chem. Commun. 1982, 23, 421; Alexander et al., Tetrahedron Lett. 1981, 22, 3711; Rao et al., Tetrahedron Lett. 1982, 23, 775; and Johnson et al., J. Am. Chem. Soc. 1981, 103, 1561.

The reported procedures suffer from a number of disadvantages. Many are lengthy, low-yield sequences which utilize starting materials that are expensive and/or not readily available. All require chromatography for isolation of various products.

A general object of the present invention, accordingly, is to provide a convenient method for the preparation of 9-acetyl-6-hydroxy-4-methoxy-7,8,9,10-tetrahydronaphthacene-5,12-dione.

Another and related object is to provide such a method which provides a relatively high overall objective-product yield.

A further related object is to provide a synthesis method which requires only one chromatographic procedure.

Still another object of the invention is to provide a novel synthesis which utilizes readily commercially available starting materials.

An additional object of the invention, related to the above objects, is to provide two novel compound "precursors" which are especially useful in the synthesis of the objective product.

In accordance with a preferred manner of practicing the invention, the proposed synthesis is characterized by conversion of 2-(2-hydroxyethyl)-bicyclo[2.2.2]octa-5-ene to 6-acetyl-4a,5,6,7,8,8a-hexahydro-1(4H)-naphthalenone (one of the important and unique "precursors" referred to above), which is reacted with 7-methoxy-3-phenylsulfonyl-1(3H)-isobenzofuranone to furnish, regiospecifically, 9-acetyl-5,12-dihydroxy-4-methoxy-6(11H)-hexahydronaphthacenone. The latter-mentioned compound is the other of the two important and unique "precursors" to the object product. Following the procedure just outlined, the hexahydronaphthacenone is transformed to tetrahydronaphthacene dione by heating the former in dimethylformamide under oxygen.

The method of the invention results in the production of the tetrahydronaphthacene dione product in 13% overall yield.

Other objects and advantages of the invention will become apparent as the same is described below in conjunction with examples which specifically illustrate the invention. In the description which follows, identical compounds are identified by like numbers which are found in the schematic representations and in the description itself.

The overall synthesis, as well as the two important "precursors", are illustrated compactly in the single drawing figure. Briefly outlining what is here shown, 2-(2-hydroxyethyl)-bicyclo[2.2.2]octa-5-ene (1a), the preparation of which has been described by Whitlock et al., J. Am. Chem. Soc. 1968, 90, 4929, and which is readily synthesized in six steps from commercially available 1,3-cyclohexadiene and ethyl acrylate, served as the starting material. Acetylation of (1a) with acetic anhydride furnished the acetate (1b). Cleavage of the olefinic entity in (1b), to give the cyclohexane dicarboxylic acid (2a), was accomplished in quantitative yield through oxidation with either ozone in acetic acid followed by subsequent workup with hydrogen peroxide, or through oxidation with a catalytic amount of insitu-generated ruthenium tetroxide, using either sodium periodate or sodium hypochlorite as a co-oxidant. The dicarboxylic acid (2a) was converted to the diacid chloride (2b) through treatment with thionyl chloride in benzene containing a catalytic amount of triethylamine. Reaction of the acid chloride (2b) with methyl copper at −20° C. in ether furnished the acetoxydiketone (2c) as an intermediate, which was hydrolyzed with sodium hydroxide to give the lactol (3). (3) was conveniently purified through recrystallization. The overall yield of (3) from (2a) is routinely 44–46%. Oxidation of (3) with chromium trioxide in pyridine furnished 1,4-diacetyl-cyclohexane-2-acetaldehyde (4), which was not purified, but directly cyclized and dehydrated to give 6-acetyl-4a5,6,7,8,8a-hexahydro-1-(4H)-naphthalenone (5) in 55% yield. Purification of (5) was achieved through chromatography followed by recrystallization. The anion of 7-methoxy-3-phenylsulfonyl-1(3H)-isobenzofuranone (6) was generated at −78° C. using lithium t-butoxide in THF and reacted with the naphthalenone (5) to furnish 9-acetyl-5,12-dihydroxy-4-methoxy-6(11H)—hexahydronaphthacenone (7) in 95% yield. Conversion of (7) to 9-acetyl-6-hydroxy-4-methoxy-7,8,9,10-tetrahydronaphthacene-5,12-dione (8) was achieved by heating (7) in dimethylformamide under oxygen at 45° C. for 18 hrs.

The object tetrahydronaphthacene dione (8), prepared by the above-described procedure in accordance with the invention, can be utilized in the production of both 11-deoxydaunorubicin, and 11-deoxyadriamycin, by first converting it to 7,9-dihydroxy-11-deoxydaunomycinone by the procedure of Johnson et al., J. Am. Chem. Soc. 1981, 103, 1561, and by then coupling this product with daunosamine, utilizing the procedure of Acton et al., J. Med. Chem. 1974, 17, 659–660.

The invention is further illustrated by way of the following detailed disclosure:

Preparation of 2-(2-acetoxyethyl)bicyclo[2.2.2]oct-5-ene (Compound 1b)

The bicyclo octenol (1a) (24.5 g, 161.0 mmol), which can be represented as follows:

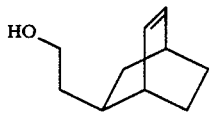

(1a)

was prepared from commercially available cyclohexadiene and ethyl acrylate, utilizing procedures described by Whitlock et al., J. Am. Chem. Soc. 1968, 90, 4929, and Narazaki et al., J. Org. Chem. 1978, 43, 4745. (1a) was added to a mixture of acetic anhydride (35 mL) and pyridine (70 mL). The reaction was stirred at room temperature overnight, diluted with ether (200 mL), and poured into water (200 mL). The ether layer was separated and successively washed with water (100 mL), 10% hydrochloric acid (2×100 mL), and saturated sodium chloride (100 mL). The ether was evaporated and the residue distilled to give 31.0 g (99% yield) of (1b) as a colorless liquid. bp 70°–72° C. (0.5 mm); $^1$H NMR (CDCl$_3$) δ6.40-6.0 (m, 2H), 4.03 (t, J=7.0 Hz, 2H), 2.60-2.18 (m, 2H), 2.03 (s, 3H), 1.84'-0.70 (m, 9H); mass spectrum, m/z 194 (M+). Anal. Calcd. for C$_{12}$H$_{18}$O$_2$ (194.26): C, 74.19; H, 9.34. Found: C, 74.44; H, 9.30.

(1b) can be represented according to the following diagram:

(1b)

Preparation of 2-(2-acetoxyethyl)cyclohexane-1,4-dicarboxylic acid (Compound 2a)

To a solution of the acetate (1b) (4.8 g, 24.7 mmol) in acetone (120 mL) was added a solution of sodium metaperiodate (26.5 g, 123.5 mmol) in water (120 mL), followed by ruthenium trichloride hydrate (50 mg). The resulting mixture was stirred at room temperature overnight. Isopropanol (5 mL) was added, and the solids which were present were removed by filtration through a celite pad. The filtrate was concentrated under reduced pressure to half of its volume. Sodium bicarbonate (5 g) was added, and the water solution was washed with ether (100 mL) which was discarded. The aqueous solution was acidified with concentrated hydrochloric acid (10 mL), and extracted with ethyl acetate (3×200 mL). The combined ethyl acetate extracts were washed with brine (100 mL), dried using (MgSO$_4$), and concentrated under reduced pressure to give 6.0 g (93% yield) of the diacid (2a) as a viscous oil. $^1$H NMR (CDCl$_3$) δ10.2 (brs, 2H), 4.15 (9t, J=7.0 Hz, 2H), 2.84-2.48 (m, 2H), 2.45-1.40 (m, 9H), 2.08 (s, 3H); mass spectrum, m/z 258 (M+). Sequential treatment of (2a) with base and acid gave the corresponding lactone with mp 165°–170° C. Anal. Calcd. for C$_{10}$H$_{14}$O$_4$ (198.21): C, 60.59; H, 7.12. Found: C, 60.54; H, 7.22.

(2a) may be represented as follows:

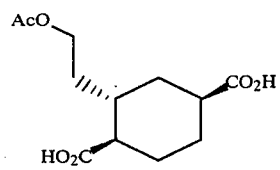

(2a)

Preparation of 2-(3-acetoxyethyl)cyclohexane-1,4-dicarboxyl chloride (Compound 2b)

To a mixture of the diacid (2a) (6.0 g, 23.3 mmol) in anhydrous benzene (60 mL) was added thionyl chloride (10 mL) and triethylamine or pyridine (3 drops). The reaction was refluxed for 3 hrs. under a nitrogen atmosphere, then evaporated at reduced pressure to give 6.5 g (95.7% yield) of the diacid chloride (2b) as a brown oil. $^1$H NMR (CDCl$_3$) δ4.40-3.95 (m, 2H), 3.40-1.40 (m, 11H), 2.08 (s, 3H); mass spectrum, m/z 295 (M+).

(2b) may be represented according to the following diagram:

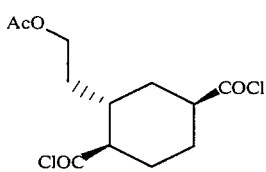

(2b)

Preparation of 2-(2-acetoxyethyl)-1,4-bis(acetyl) cyclohexane (Compound 2c)

To a suspension of dry cuprous iodide (38.6 g, 200.0 mmol) in anhydrous ether (900 mL) at −40° C. under a nitrogen atmosphere was added, with stirring, a solution of methyllithium (143 mL of 1.4 M, 200 mmol). The ether solution of methyl copper was stirred for 15 min., at which time the acid chloride (2b) (13.4 g, 45 mmol) was slowly added. The reaction mixture was allowed to come to ambient temperature, then quenched with saturated ammonium chloride solution (400 mL). The ether layer was separated, and the aqueous layer was extracted with ether (300 mL). The organic phases were combined, dried using (MgSO$_4$), and concentrated to give 8.5 g (74%) of diketone (2c) as a yellowish oil which was used in the next step without further purification. $^1$H NMR δ4.09 (t, J=6 Hz, 2H), 3.0-2.64 (m, 2H), 2.14 (s, 3H), 2.13 (s, 3H), 2.04 (s, 3H), 2.0–1.2 (m, 9H); mass spectrum, m/z 254 (M+).

(2c) can be represented by the following:

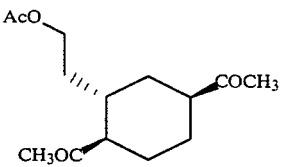

(2c)

Preparation of 6-acetyl-1-hydroxy-1-methyl-3,4,4a,5,6,7,8,8a-octahydro-1H-2-benzopyran (Compound 3)

To a solution of (2c) (8.5 g, 33.5 mmol) in methanol (60 mL) was slowly added a solution of sodium hydroxide (4.0 g) in water (60 mL). The resulting mixture was stirred at ambient temperature for 1 hr., then evaporated at reduced pressure to remove most of the methanol. The basic aqueous solution was extracted with ether (4×200 mL), and the combined ether extracts were washed with brine (50 mL), then dried using (MgSO$_4$), and concentrated at reduced pressure to give (3)—a pale yellow solid. Recrystallization of this material from ethylacetatehexane furnished 4.2 g (59.1% yield) of alcohol (3): mp 115°-116° C., $^1$H NMR (CDCl$_3$) δ4.16-3.50 (m, 3H), 2.60-2.20 (m, 1H), 2.14 (s, 3H), 2.0–1.8 (m, 10H), 1.39 (s, 3H); mass spectrum, m/z 212 (M+). Anal. Calcd. for C$_{12}$H$_{20}$O$_3$ (212.28): C, 67.89; H, 9.50. Found: C, 67.70; H, 9.50.

Compound (3) can be visualized according to the following diagram:

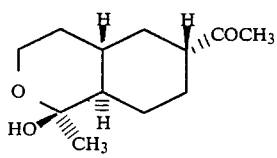

(3)

Preparation of 6-acetyl-4a,5,6,7,8,8a-hexahydro-1-(4H)-naphthalenone (Compound 5)

To a well stirred suspension of pyridinium chlorochromate (14.8 g, 68.5 mmol) in anhydrous methylene chloride (130 mL) was added a solution of alcohol (3) (2.9 g, 13.7 mmol) in anhydrous methylene chloride (20 mL). The resulting mixture was stirred at room temperature overnight, at which time the methylene chloride was decanted from the solids which were present. The solid residue was washed with ether, and the ether washing was combined with the methylene chloride, then dried using (MgSO$_4$), filtered and evaporated at reduced pressure to furnish 2.1 g (73% yield) of 2-(2,5-diacetylcyclohexane)-acetaldehyde (4). $^1$H NMR (CDCl$_3$) δ10.32 (brs, 1H), 2.64-1.80 (m, 11H), 2.16 (s, 6H); mass spectrum, m/z 210 (M+).

(4) may be represented schematically as follows:

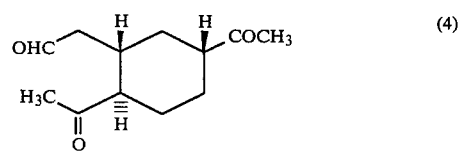

(4)

The acetaldehyde intermediate (4) (2.1 g, 10 mmol) was taken up in tetrahydrofuran (200 mL), and water (0.5 mL) and concentrated hydrochloric acid (1.0 mL) were added. The solution was heated at reflux for 5 hrs., then diluted with water (20 mL) and evaporated at reduced pressure to remove most of the tetrahydrofuran. The residual aqueous solution was extracted with ether (3×200 mL), and the combined ether extracts were successively washed with saturated sodium bicarbonate solution (20 mL), brine (50 mL), then dried and concentrated to give a semisolid. Recrystallization from benzene hexane provided 1.0 g (52.1%) of compound (5). mp 86°-91° C., $^1$H NMR (CDCl$_3$) δ7.04-6.78 (m, 1H), 6.12-5.84 (m, 1H), 2.60-1.0 (m, 11H), 2.16 (s, 3H); mass spectrum, m/z 192 (M+).

(5) can be represented according to the following diagram:

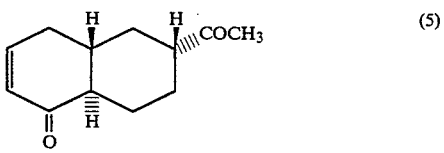

(5)

Preparation of 9-acetyl-5,12-dihydroxy-4-methoxy-6-(11H)-hexahydro-naphthacenone (Compound 7)

To a magnetically stirred solution of lithium t-butoxide (8.8 mmol, prepared from 8.8 mmol of n-BuLi and 9.0 mmol of t-BuOH in 100 mL of THF), cooled to −78° C., was slowly added a slurry of 7-methoxy-3-phenylsulfonyl-1-(3H)-isobenzofuranone (6) (0.91 g, 3 mmol) in THF (20 mL).

(6) may be represented as follows:

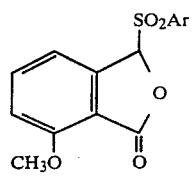

After stirring the resulting solution for 5 min., (5) (0.9 g, 4.7 mmol) was added and the reaction mixture was stirred at the same temperature (−78° C.) for 10 min. The cooling bath was removed, and the reaction mixture was stirred at the ambient temperature for 1 hr., then acidified with 2 mL of 6N HCl, whereupon bright yellow crystals of (7) precipitated out. The crystals were collected by filtration washed with $CH_2Cl_2$ (50 mL) to furnish 0.98 g (92.5% yield) of pure 9-acetyl-5,12-dihydroxy-4-methoxy-6(11H)-hexahydronaphthacenone (7). mp 223°–226° C.; mass spectrum, m/z 354 (M+). Compound (7) was found to be extremely sensitive to air oxidation, and satisfactory combustion analyses could not be obtained. The observation that (7) was air sensitive was utilized to oxidize it to (8).

(7) can be represented as follows:

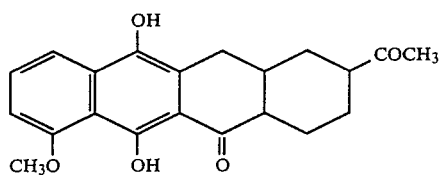

Preparation of 9-acetyl-6-hydroxy-4-methoxy-7,8,9,10-tetrahydronaphthacene-5,12-dione (Compound 8)

A solution of (7) (0.4 g, 1.1 mmol) in dimethylforamide (40 mL) was heated at 110° C. Simultaneously, oxygen was bubbled through it. After 2 hrs., flow of oxygen was terminated and 2 mL of water was added. Upon cooling, the reaction mixture gave orange crystals of (8).

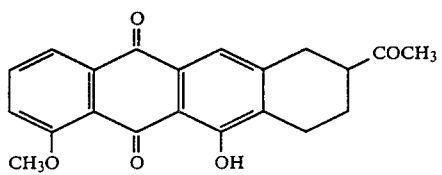

These crystals were collected by filtration, washed with water and dried: yield 0.37 g (94% yield) of (8) with mp 222°–225° C. (lit. mp 223°–226° C.), $^1H$ NMR ($CDCl_3$) δ 13,36 (s, 1H), 8.08-7.22 (m, 4H), 4.07 (s, 3H), 3.30-2.40 (m, 4H), 2.27 (s, 3H), 2.27 (m, 1H), 2.0-1.4 (m, 2H), mass spectrum, m/z 350 ($M^{30}$). Anal. Calcd. for $C_{21}H_{18}O_5$ (350.35): C, 71.99; H, 5.18. Found: C, 71.70; H, 5.30.

It is claimed and desired to secure as letters patent:

1. The compound having the formula

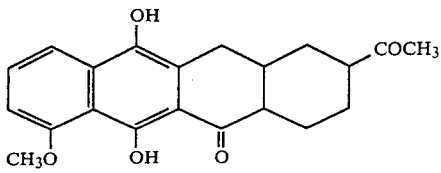

2. A method for synthesizing the compound having the formula

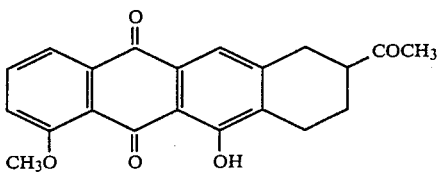

which comprises
converting 2-(2-hydroxyethyl)bicyclo[2.2.2.]oct-5-ene to a hexahydronaphthalenone product having the formula

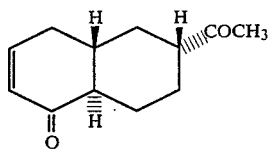

through the steps of acetylizing the bicyclooctene to furnish 2-(2-acetoxyethyl)bicyclo[2.2.2.]oct-5-ene, cleaving the olefinic entity in the latter to give 2-(2-acetoxyethyl)cyclohexane-1,4-dicarboxylic acid, converting the dicarboxylic acid to 2-(3-acetoxyethyl)cyclohexane-1,4-dicarboxyl chloride, reacting the latter with methyl copper to furnish the acetoxydiketone 2-(2-acetoxyethyl)-1,4-bis-(acetyl)-cyclohexane, hydrolyzing the acetoxydiketone to give the lactol 6-acetyl-1-hydroxy-1-methyl-3,4,4a,5,6,7,8,8a-octahydro-1H-2-benzopyran, oxidizing the lactol to produce 1,4-diacetyl-cyclohexane-2-acetaldehyde, and cyclizing and dehydrating the latter compound to yield the above-pictured hexahydronaphthalenone product, reacting the hexahydronaphthalenone product with phenylsulfonyl isobenzofuranone to create a hexahydronaphthacenone product having the formula

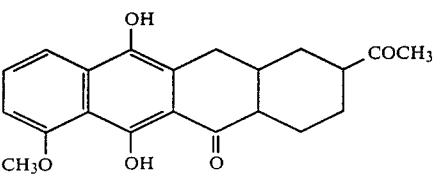

and heating the hexahydronaphthacenone product in dimethylforamide under an oxygen atmosphere to produce the object compound.

3. A method starting from bicyclooctene for synthesizing the compound having the formula

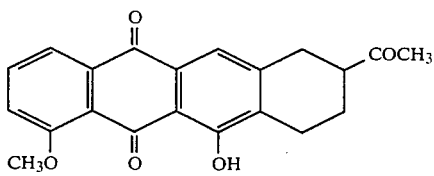

which comprises
converting bicyclooctene to a hexahydronaphthalenone product having the formula

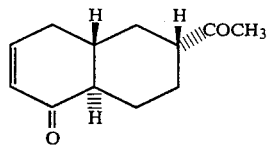

through the steps of acetylizing the bicyclooctene to furnish 2-(2-acetoxyethyl)bicyclo [2.2.2.]oct-5-ene, cleaving the olefinic entity in the latter to give 2-(2-acetoxyethyl)cyclohexane-1,4-dicarboxylic acid, converting the dicarboxylic acid to 2-(3-acetoxyethyl)cyclohexane-1,4-dicarboxyl chloride, reacting the latter with methyl copper to furnish the acetoxydiketone 2-(2-acetoxyethyl)-1,4-bis-(acetyl)-cyclohexane, hydrolyzing the acetoxydiketone to give the lactol 6-acetyl-1-hydroxy-1-methyl-3,4,4a,5,6,7,8,8a-octahydro-1H-2-benzopyran, oxidizing the lactol to produce 1,4-diacetyl-cyclohexane-2-acetaldehyde, and cyclizing and dehydrating the latter compound to yield the above-pictured hexahydronaphthalenone product, reacting the hexahydronaphthalenone product with phenylsulfonyl isobenzofuranone to create a hexahydronaphthacenone product having the formula

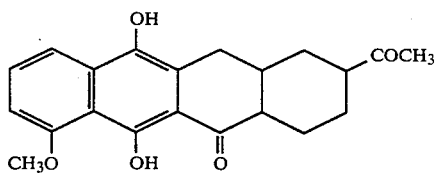

and heating the hexahydronaphthacenone product in dimethylforamide under an oxygen atmosphere to produce the compound.

* * * * *